(12) United States Patent
Ratjen

(10) Patent No.: US 12,329,941 B2
(45) Date of Patent: Jun. 17, 2025

(54) MEDICAMENT DELIVERY DEVICE

(71) Applicant: SHL MEDICAL AG, Zug (CH)

(72) Inventor: Jochen Ratjen, Nacka (SE)

(73) Assignee: SHL Medical AG, Zug (CH)

( * ) Notice: Subject to any disclaimer, the term of this patent is extended or adjusted under 35 U.S.C. 154(b) by 1002 days.

(21) Appl. No.: 17/293,161

(22) PCT Filed: Nov. 20, 2019

(86) PCT No.: PCT/EP2019/081925
§ 371 (c)(1),
(2) Date: May 12, 2021

(87) PCT Pub. No.: WO2020/126270
PCT Pub. Date: Jun. 25, 2020

(65) Prior Publication Data
US 2022/0008655 A1 Jan. 13, 2022

(30) Foreign Application Priority Data
Dec. 20, 2018 (EP) .................................. 18214963

(51) Int. Cl.
*A61M 5/24* (2006.01)
*A61M 5/20* (2006.01)
*A61M 5/32* (2006.01)

(52) U.S. Cl.
CPC ........ *A61M 5/2448* (2013.01); *A61M 5/2033* (2013.01); *A61M 5/2046* (2013.01);
(Continued)

(58) Field of Classification Search
CPC .............. A61M 5/2448; A61M 5/2033; A61M 5/2046; A61M 5/3202; A61M 2005/2451;
(Continued)

(56) References Cited

U.S. PATENT DOCUMENTS

| 6,893,420 B2 | 5/2005 | Arnisolle |
| 2011/0251553 A1* | 10/2011 | Ratjen ................. A61M 5/2066 604/89 |

(Continued)

FOREIGN PATENT DOCUMENTS

| CN | 108290000 A | 7/2018 |
| EP | 2326367 A1 | 6/2011 |

(Continued)

OTHER PUBLICATIONS

International Search Report and Written Opinion for Int. App. No. PCT/EP2019/081925, mailed Dec. 13, 2019.

*Primary Examiner* — Kami A Bosworth
*Assistant Examiner* — Avery Smale
(74) *Attorney, Agent, or Firm* — McDonnell Boehnen Hulbert & Berghoff LLP

(57) ABSTRACT

A medicament delivery device is presented having a housing with a proximal end and a distal end, a multi-chamber container arranged in the housing, a power assembly having accumulated energy arranged in the housing and configured to act on the multi-chamber container for obtaining and delivering a blended compound inside the multi-chamber container and a manually operable assembly extending from the distal end of the housing and being connected with the power assembly, wherein upon a manual movement of the manually operable assembly the power assembly is forced to move towards the proximal end to pressurize the multi-chamber container and wherein the medicament delivery device further comprises a needle shield sleeve slidably arranged in the housing, the needle shield sleeve being configured to interact with the power assembly to release the accumulated energy after the power assembly has been moved towards the proximal end.

19 Claims, 7 Drawing Sheets

(52) U.S. Cl.
CPC ... *A61M 5/3202* (2013.01); *A61M 2005/2451* (2013.01); *A61M 2005/2474* (2013.01); *A61M 2005/3268* (2013.01)

(58) Field of Classification Search
CPC .. A61M 2005/2474; A61M 2005/3268; A61M 5/19; A61M 5/2455; A61M 5/284; A61M 5/288; A61M 5/3243; A61M 5/326; A61M 2005/2013; A61M 2005/2026; A61M 2005/3267; A61M 5/2066; A61M 2005/2073; A61M 5/20; A61M 2005/206; A61M 2005/208; A61M 5/24
See application file for complete search history.

(56) References Cited

U.S. PATENT DOCUMENTS

| | | | |
|---|---|---|---|
| 2012/0253274 A1 | 10/2012 | Karlsson et al. | |
| 2012/0265136 A1* | 10/2012 | Lawlis | A61M 5/31553 604/110 |
| 2014/0371670 A1 | 12/2014 | Holmqvist | |
| 2016/0287791 A1 | 10/2016 | Olson | |
| 2017/0304548 A1* | 10/2017 | Chen | A61M 5/3202 |
| 2018/0200442 A1* | 7/2018 | Atterbury | A61M 5/326 |

FOREIGN PATENT DOCUMENTS

| | | |
|---|---|---|
| JP | 2013-530024 A | 7/2013 |
| JP | 2016-500321 A | 1/2016 |
| JP | 2018-522684 A | 8/2018 |
| WO | 2012/003516 A2 | 1/2012 |
| WO | 2017/027876 A1 | 2/2017 |

* cited by examiner

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2019/081925 filed Nov. 20, 2019, which claims priority to European Patent Application No. 18214963.3 filed Dec. 20, 2018. The entire disclosure contents of these applications are herewith incorporated by reference into the present application.

TECHNICAL FIELD

Provided is a medicament delivery device having an initial locked state, an intermediate mixing state, and a medicament delivery state.

BACKGROUND

One solution for keeping a medicament delivery device as pre-assembled as possible is to deliver the medicament delivery device with a delivery member, such as a needle, pre-attached. This solution often causes the rear end of the needle to protrude into the interior of the container, which could be a drawback if the medicament reacts with the material of the delivery member when exposed for a period of time. In that respect and especially when having multi-chamber containers, it is desirable to have the rear part of the delivery member outside the container until a mixing is to be performed. To avoid foaming or jeopardizing the mixing of sensitive medicament components, the mixing has to be performed at a slow rate. Also, to minimize the number of actions needed in order to perform a safe injection where the needle is always out of range for a user, some devices only need to be pressed against the injection area, without the need of touching or seeing the needle and of injecting by pressing a button or the like, which causes the needle to penetrate the injection area and the device to perform the injection.

A disadvantage of prior art solutions is that they sometimes are unreliable, non-suitable where the needle has to be non-visible and unreachable for the user, non-suitable where the mixing has to be achieved at a slow rate, and may unintentionally be actuated. U.S. Pat. No. 6,893,420 discloses a device arranged with a locking means for locking a ledge that prevents the automatic penetration and injection means from being released before mixing of the medicament is finished. However, this device suffers from the disadvantage of a user having to remove the locking means actively from the device after the mixing is finished, thereby causing an unnecessary step which may be disadvantageous, and especially considering emergency usage of such device.

SUMMARY

In view of the above an objection is to provide a medicament delivery device that is suitable for slow rate mixing, safe to use and that is easy to use when handling.

There is hence provided a medicament delivery device comprising: a housing having a proximal end and a distal end; a multi-chamber container arranged in the housing; a power assembly having accumulated energy, arranged in the housing and configured to act on the multi-chamber container for obtaining and delivering a blended compound inside the multi-chamber container; a manually operable assembly extending from the distal end of the housing and being connected with the power assembly, wherein upon a manual movement of the manually operable assembly the power assembly is forced to move towards the proximal end to pressurise the multi-chamber container; wherein the medicament delivery device further comprises a needle shield sleeve slidably arranged in the housing, the needle shield sleeve being configured to interact with the power assembly to release the accumulated energy after the power assembly has been moved towards the proximal end.

A user does hence not have to actively remove locking means from the device after the mixing is finished to actuate the device. The operation of the medicament delivery device may thereby be simplified.

According to one embodiment the power assembly is a gas, electromechanical or spring driven power assembly.

According to one embodiment the manually operable assembly is connected with the power assembly by a threaded connection.

According to one embodiment the manual movement of the manually operable assembly is a rotational movement and the threaded connection is configured to cause linear movement of the power assembly towards the proximal end.

In another embodiment the manually operable assembly is connected with the power assembly by a known connection in the art such that a rotational movement of the manually operable assembly causes a rotational movement of the power assembly towards the proximal end.

In a further embodiment the manually operable assembly is connected with the power assembly by a known connection in the art such that a linear movement of the manually operable assembly causes a rotational movement of the power assembly towards the proximal end.

In another embodiment the manually operable assembly is connected with the power assembly by a known connection in the art such that a linear movement of the manually operable assembly causes a linear movement of the power assembly towards the proximal end.

One embodiment comprises a container holder fixedly connected to the housing and in which the multi-chamber container is accommodated, and a resilient member arranged between the proximal end of the container holder and a proximal inner ledge of the needle shield sleeve.

One embodiment comprises a needle assembly disposed on a proximal end of the container holder and having a needle, wherein the multi-chamber container has a septum, and wherein the needle assembly is configured to be manually manipulated to move the needle toward the multi-chamber container in order for a distal end of the needle to pierce the septum.

According to one embodiment the needle assembly comprises:—a needle hub fixedly connected to the needle;—an inner cap configured to move the needle hub;—a retainer fixedly connected to the container holder and interactively engaged with the needle hub;—a manually operable outer cap configured to move the inner cap whereby the inner cap in turn moves the needle hub through the retainer and toward the multi-chamber container in order for the distal end of the needle to pierce the septum and whereby the inner cap together with outer cap can be removed from the medicament delivery device.

According to one embodiment the manually operable outer cap is configured to lock the needle shield sleeve in an initial locked position in which the needle shield sleeve is prevented from being axially moveable by the bias of the resilient member towards the proximal end of the device to an initial unlocked position.

According to one embodiment a member on the distal end of the needle shield sleeve is releasably locked to a member of the manually operable assembly when the needle shield sleeve is in the initial locked position for preventing the manually operable assembly to be manually operated. A user is thereby prevented to accidentally perform a mixing operation as long as the needle shield sleeve is in the initial locked position.

According to one embodiment upon removal of the manually operable outer cap from the medicament delivery device, the needle shield sleeve is forced by the bias of the resilient member to move a predetermined distance in relation to the housing from its initial locked position to an initial unlocked position in which a predetermined portion of the needle shield sleeve protrudes from the proximal end of the housing.

According to one embodiment upon a movement of the needle shield sleeve in relation to the housing from its initial unlocked position towards the distal end of the housing allows a member on the distal end of the needle shield sleeve to interact with a member of the power assembly to release the accumulated energy in the power assembly.

According to one embodiment the multi-chamber container comprises a stopper and the power assembly comprises a plunger rod configured to be in contact with the distal surface of the stopper.

According to one embodiment the power assembly further comprises a holding and release unit configured to interact with the plunger rod and the needle shield sleeve for holding and releasing the accumulated energy in the power assembly.

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

Throughout the description and claims of this specification, the words "comprise" and "contain" and variations of the words, for example "comprising" and "comprises", means "including but not limited to", and is not intended to (and does not) exclude other components, integers or steps.

Further, throughout the description and claims of this specification, the singular encompasses the plural unless the context otherwise requires. In particular, where the indefinite article is used, the specification is to be understood as contemplating plurality as well as singularity, unless the context requires otherwise.

The medicament delivery device may have an initial locked state, an intermediate priming state, and a medicament delivery state.

The medicament delivery device may for example be an injector, in particular an auto-injector, an inhaler or an eye dispenser.

BRIEF DESCRIPTION OF THE DRAWINGS

Examples of the inventive concept will now be described, by way of example, with reference to the accompanying drawings, in which.

DETAILED DESCRIPTION

Figure 1:
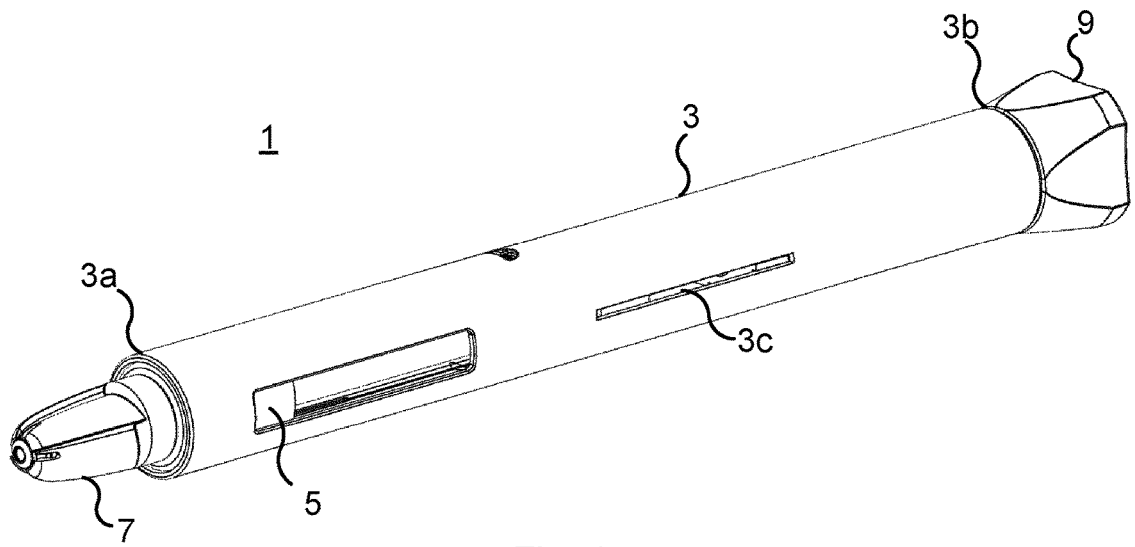
FIG. 1 is a perspective view of an example of a medicament delivery device in an initial locked state.

FIG. 1 shows an example of a medicament delivery device 1. The exemplified medicament delivery device 1 is a mixing type of medicament delivery device. To this end, the medicament delivery device 1 is configured for mixing of a freeze-dried/powered medicament with a liquid.

The medicament delivery device 1 comprises an elongated hollow housing 3. The housing 3 has a proximal end 3a and a distal end 3b. The exemplified housing 3 furthermore has guide slits 3c, of which one is visible in FIG. 1. The medicament delivery device 1 furthermore comprises a needle shield sleeve 5 configured to be received by the housing 3. The needle shield sleeve 5 is configured to move linearly relative to the housing 3. The needle shield sleeve 5 is biased in the proximal direction, i.e. in a direction from the distal end 3b towards the proximal end 3a. The needle shield sleeve 5 is rotationally locked relative to the housing 3.

In the initial locked state of the medicament delivery device 1, the needle shield sleeve 5 is fully received or essentially fully received by the housing 3. The medicament delivery device 1 furthermore comprises an outer cap 7, which in the initial locked state of the medicament delivery device 1 is mounted such that it causes the needle shield sleeve 5 to be fully or essentially fully received by the housing 3.

The medicament delivery device 1 also includes a mixing knob 9 which extends in the distal direction, i.e. in a direction from the proximal end 3a towards the distal end 3b, from the distal end 3b of the housing 3. The mixing knob 9 is in the initial locked state of the medicament delivery device 1 rotationally locked relative to the housing 3. In an intermediate priming state, described in more detail below, of the medicament delivery device 1, the mixing knob 9 may be rotated relative to the housing 3. Mixing of a medicament contained inside the housing 3 may thereby be provided.

Figure 2:
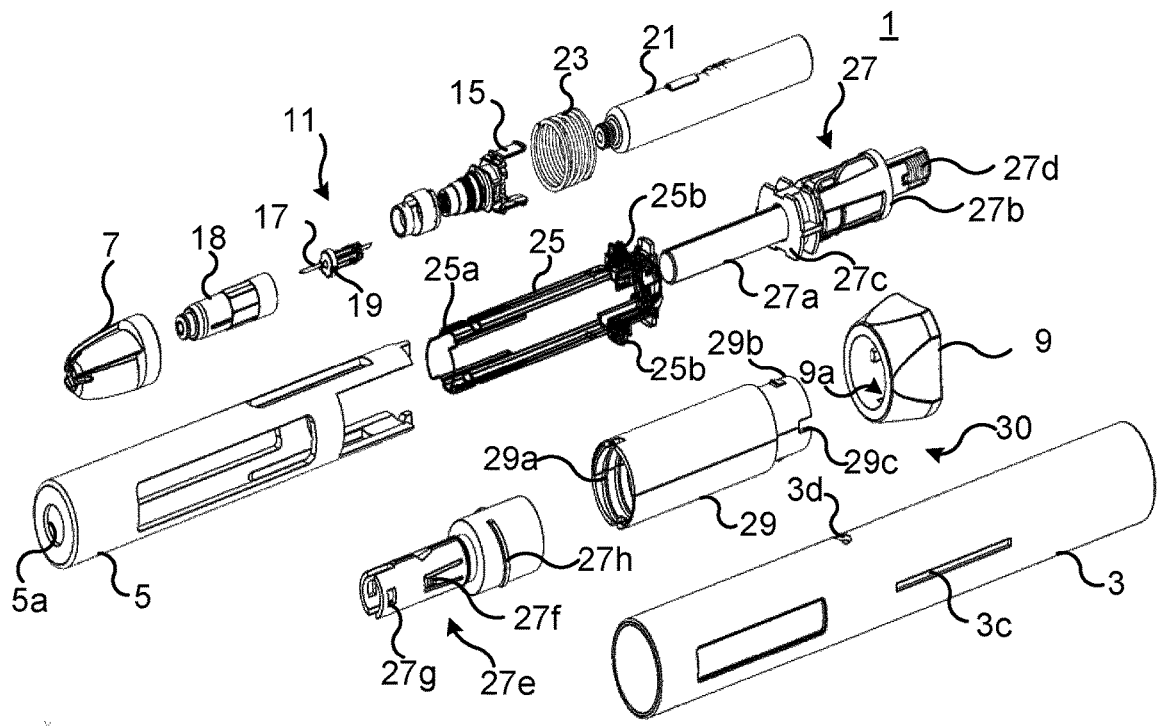
FIG. 2 is an exploded view of the medicament delivery device in FIG. 1.

FIG. 2 is an exploded view of the medicament delivery device 1 depicted in FIG. 1. The medicament delivery device 1 furthermore comprises a needle assembly 11, which includes the outer cap 7, an inner cap 13, a retainer 15, a double-sided needle 17, and a needle hub 19 fixedly connected to the needle 17.

The medicament delivery device 1 comprises a multi-chamber container 21, a resilient member 23, such as a spring, configured to bias the needle shield sleeve 5 in the proximal direction, and a container holder 25 configured to accommodate the multi-chamber container 21. The resilient member 23 is arranged between a proximal end 25a of the container holder 25 and a proximal inner ledge 5a of the needle shield sleeve 5. The container holder 25 is configured to be axially and rotationally locked relative to the housing 3. The housing 3 has radial openings 3d, of which one is visible in FIG. 2. The container holder 25 has radially outwards extending locking members 25a configured to engage with a respective one of the radial openings 3d to thereby lock the container holder 25 to the housing 3.

The medicament delivery device 1 furthermore comprises a power assembly 27. The power assembly 27 is configured to be received by the housing 3. The power assembly 27 comprises a plunger rod 27a, a hollow rotator 27b through which the plunger rod 27a extends, a guide member 27c arranged proximally relative to the rotator 27b and arranged around the plunger rod 27a, and a resilient member 27d extending longitudinally inside the plunger rod 27a. The resilient member 27d, such as a spring, is configured to bias the plunger rod 27a in the proximal direction, towards the proximal end 3a of the housing 3.

The power assembly 27 furthermore comprises a holding and release unit 27e configured to partly be received radially between the rotator 27b and the plunger rod 27a. The holding and release unit 27e is provided with flexible radially inwards extending arms 27f and the plunger rod 27a has corresponding radial openings (not shown) configured to receive a respective one of the arms 27f to hold the plunger rod 27a axially. The arms 27f are biased radially outwards. The rotator 27b, which surrounds a portion of the holding and release unit 27e, in particular the portion provided with the arms 27f, has an inner surface which urges the arms 27f radially inwards such that they engage with the radial openings of the plunger rod 27a. The plunger rod 27a is thereby locked axially by the holding and release unit 27e. The rotator 27b is configured to rotate relative to the plunger rod 27a, in particular by interaction with the needle shield sleeve 5. The inner surface of the rotator 27b facing the holding and release unit 27e is provided with recesses such that when the rotator 27b is rotated the recesses align with a respective one of the arms 27f, enabling the arms 27f to flex radially outwards and thereby release the plunger rod 27b from its engagement with the holding and release unit 27e. The plunger rod 27b will consequently move in the proximal direction towards the proximal end 3a of the medicament delivery device 1 and further into the multi-chamber container 21 to thereby cause medicament expulsion from the multi-chamber container 21.

The holding and release unit 27e is configured to engage with the guide member 27c. The holding and release unit 27e has radial openings 27g configured to engage with corresponding radial inwards extending protrusions (not shown) of the guide member 27c. The holding and release unit 27e and the guide member 27c are axially and rotationally locked with each other.

The medicament delivery device 1 comprises a sleeve member 29. The sleeve member 29 and the mixing knob 9 form a manually operable assembly 30. The sleeve member 29 is provided with a first thread structure 29a. In particular, the inner surface of the sleeve member 29 is provided with the first thread structure 29a. The sleeve member 29 is configured to receive a distal portion of the holding and release unit 27e. The distal portion of the holding and release unit 27e is provided with an external second thread structure 27h. The first thread structure 27h and the second thread structure 29a form a threaded connection between the sleeve member 29 and the holding and release unit 27e and hence between the power assembly 27 and the manually operable assembly 30.

The mixing knob 9 is configured to be fitted on a distal end portion 29b of the sleeve member 29. The mixing knob 9 is configured to be engaged with the sleeve member 29. The mixing knob 9 and the sleeve member 29 are configured to be axially and rotationally locked relative to each other. Rotation of the mixing knob 9 hence causes rotation of the sleeve member 29. The mixing knob 9 and the sleeve member 29 may for example be provided with corresponding rotation locking elements 29, such as axial ribs and corresponding axial recesses to prevent relative rotation between these components. The mixing knob 9 and the sleeve member 29 may also be provided with axially locking elements to lock the mixing knob 9 axially relative to the sleeve member 29.

Figure 3:
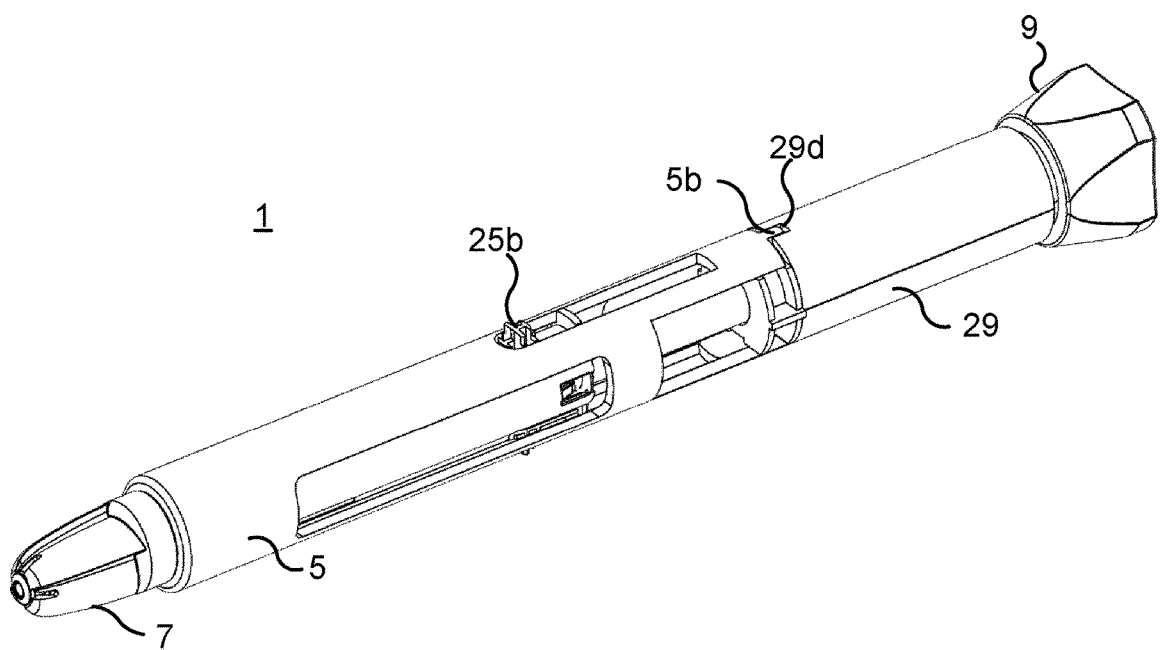
FIG. 3 is a perspective view of the medicament delivery device in FIG. 1 with the housing removed.

FIG. 3 shows the medicament delivery device 1 in the initial locked state with the housing 3 removed to expose the interior of the medicament delivery device 1. In this position, the needle shield sleeve 5 is in an initial locked position relative to the housing 3. In particular, the needle shield sleeve 5 is pushed into and maintained in the housing 3 by the outer cap 7, which is fitted to the retainer 15.

The needle shield sleeve 5 has a distal end provided with a member locked to a member of the manually operable assembly 30. In particular, the distal end of the needle shield sleeve 5 is provided with axial protrusions 5b and the sleeve member 29 is provided with corresponding axial recesses 29d configured to receive a respective axial protrusion 5b. The needle shield sleeve 5 is thereby rotationally locked relative to the sleeve member 29 and hence relative to the manually operably assembly 30.

Figure 4:
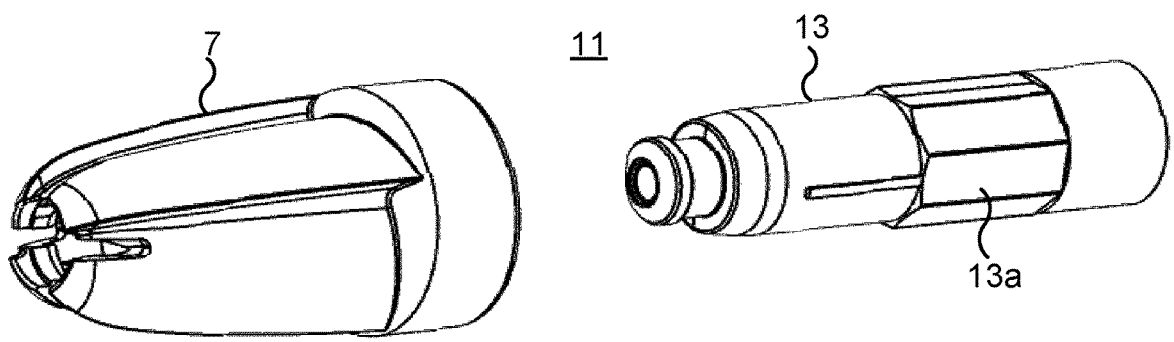
FIG. 4 shows a perspective view of a needle assembly.
Figure 4:
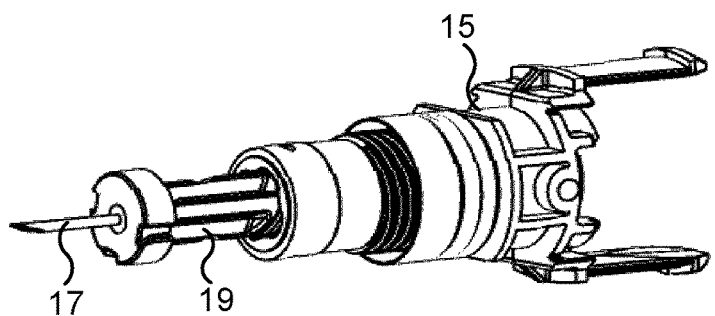

FIG. 4 shows the needle assembly 11. The outer cap 7 has an inner polygonal surface portion configured to engage with a corresponding outer polygonal surface portion 13a of the inner cap 13. In the initial locked state of the medicament delivery device 1 the inner cap 13 is mounted to the retainer 15 and the outer cap 7 is mounted to the inner cap 13. Since the relatively large outer cap 7 is assembled with the retainer 15 which normally is covered by the needle shield sleeve 5 which is biased in the proximal direction by the resilient member 23, the needle shield sleeve 5 is pushed somewhat into the housing 3 by the outer cap 7. The needle shield sleeve 5 is hence axially locked relative to the housing 3 in the initial locked position of the needle shield sleeve 5.

When the outer cap 7 is unscrewed, the inner cap 13 is brought with it. Additionally, while the outer cap 13 is being unscrewed, the needle hub 19, including the double-edged needle 17 is screwed in the distal direction to pierce a septum in the retainer and/or the multi-chamber container 21. The needle shield sleeve 5 is due to its biased state moved from its initial locked position in the proximal direction, out from the housing 3, when the outer cap 13 holding the needle shield sleeve 5 in the initial locked position has been unscrewed. The needle shield sleeve 5 thereby obtains an initial unlocked position. The medicament delivery device 1 hence obtains an intermediate priming state, in which the medicament delivery device 1 is ready for mixing. Since the needle shield sleeve 5 is moved in the proximal direction the axial protrusions 5b are moved out from their engagement with the axial recesses 29d of the sleeve member 9, and hence the mixing knob 9 and the sleeve member 29, i.e. the manually operable assembly 30, become rotatable relative to the housing 3.

Figure 5:
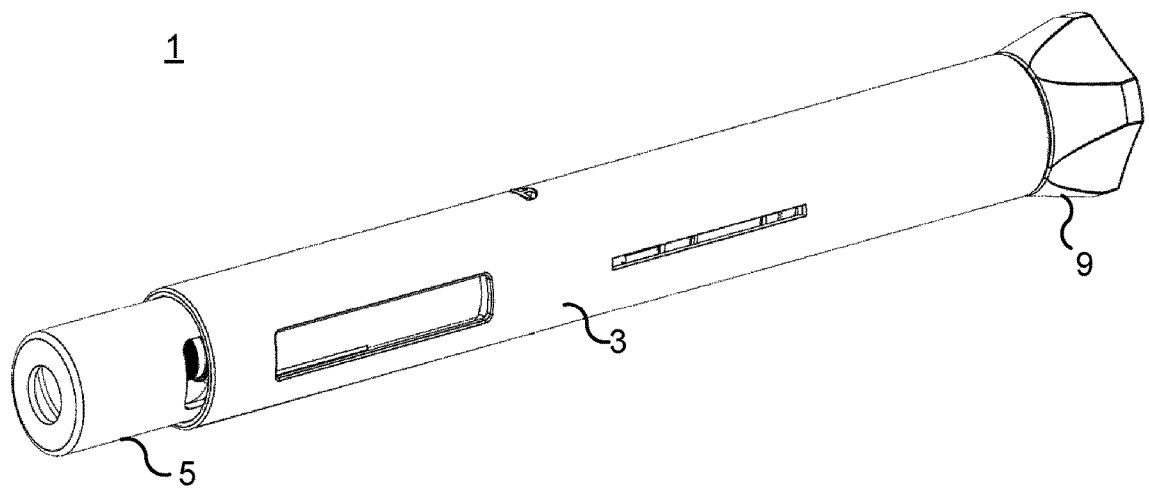
FIG. 5 is a perspective view of the medicament delivery device in an intermediate priming state.

FIG. 5 shows the medicament delivery device 1 in the intermediate priming state with the needle shield sleeve 5 extending proximally from the housing 3.

Figure 6:
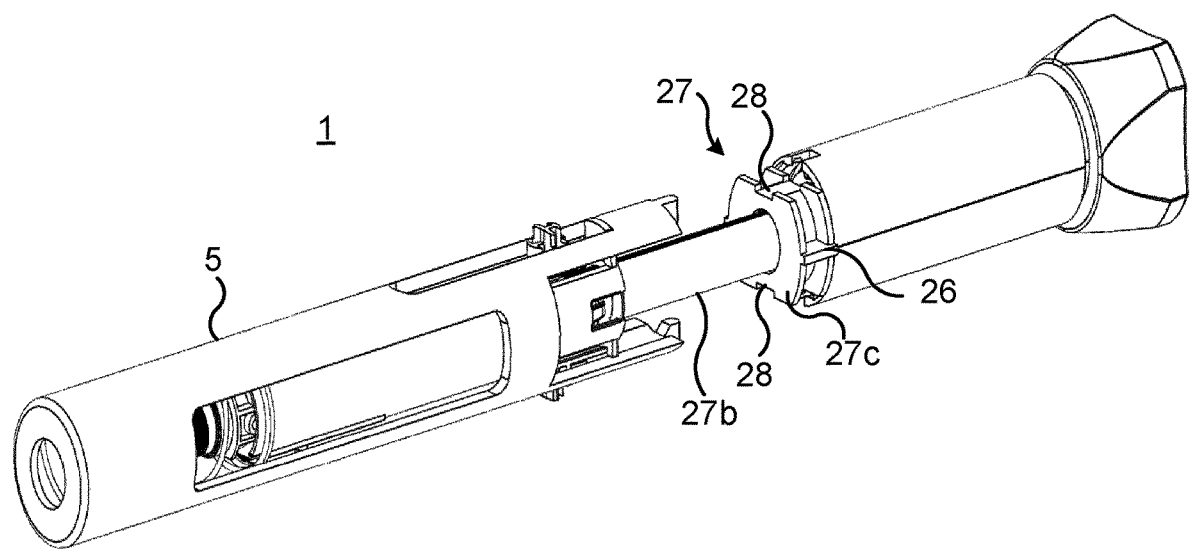
FIG. 6 is a perspective view of the medicament delivery device in FIG. 5 with the housing removed.

FIG. 6 shows the medicament delivery device 1 with the housing 3 removed to expose the interior of the medicament delivery device 1 in the intermediate priming state. In this state, the needle shield sleeve 5 is distanced far apart from the guide member 27c and the power assembly 27. The distance is such that manipulation of the needle shield sleeve 5, i.e. movement of the needle shield sleeve 5 into the housing 3 will not result in any interaction of the needle shield sleeve 5 with the power assembly 27, and in particular with the rotator 27b. The guide member 27 furthermore has axial guide grooves 28 configured to guide the needle shield sleeve 5 when the needle shield sleeve 5 is moved in the distal direction after the mixing procedure has been performed. In particular, the guide grooves 28 are configured to receive the axial protrusions 5b at the proximal end of the needle shield sleeve 5 and guide the needle shield sleeve 5 so that it becomes properly aligned with the rotator 27b to interact with the rotator 27b and cause rotation of the rotator 27b to thereby release the plunger rod 27a.

The guide member 27c is rotationally locked with the holding and release unit 27e. The guide member 27c is furthermore rotationally locked relative to the housing 3. The guide member 27c has radially outwards extending guide structures 26 configured to engage with a respective one of the guide slits 3c of the housing 3 to thereby allow axial movement of the power assembly 27 as the guide structures 26 slide in the proximal direction in the guide slits 3c, while preventing rotation thereof relative to the housing 3. Thus, a rotation movement of the manually operable assembly 30 causes a linear movement of the power assembly 27 towards the proximal end 3a. Moreover, the guide structures 26 serve as mixing state indicators or visual feedback to the user, since the structures 26 can be seen through the guide slits 3c of the housing 3. The housing 3 may have printings/indicia or may be arranged with a label having indicators/indicia that indicate or give feedback to the user of the different positions of the guide structures 26. It is also feasible that the structures 26 may be locked to the proximal end of the guide slit 3c.

It may also be feasible that the manually operable assembly is connected with the power assembly by known connections in the art such that: —a rotational movement of the manually operable assembly causes a rotational movement of the power assembly towards the proximal end, —a linear movement of the manually operable assembly causes a rotational movement of the power assembly towards the proximal end, —a linear movement of the manually operable assembly causes a linear movement of the power assembly towards the proximal end.

Figure 7:
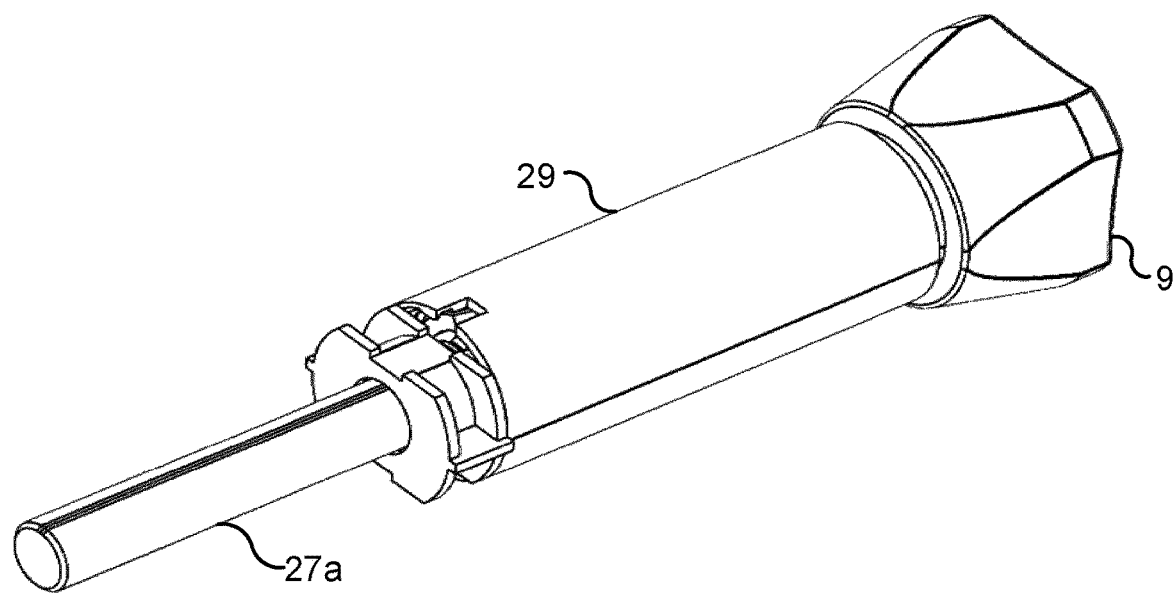
FIG. 7 is shows a manually operable assembly and a power assembly of the medicament delivery device in FIG. 1.
Figure 8:
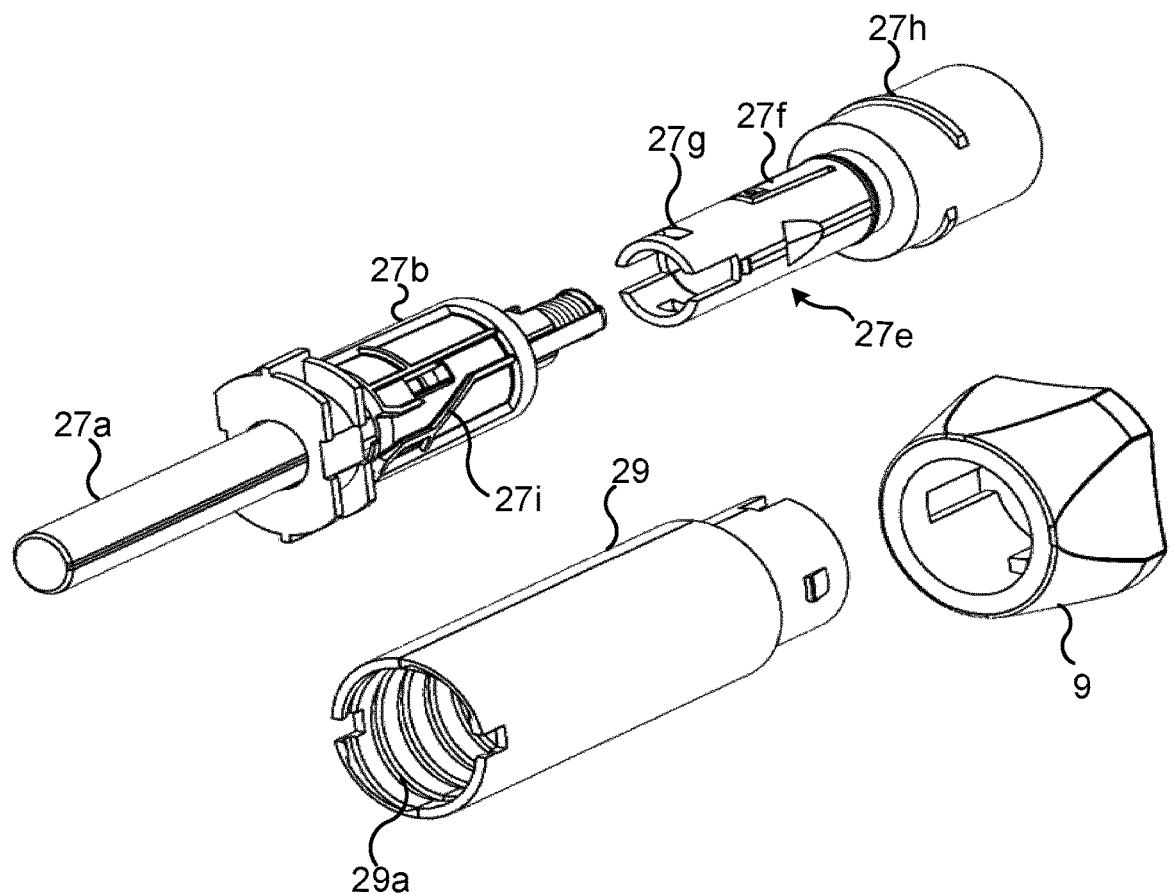
FIG. 8 is an exploded view of the manually operable assembly and the power assembly in FIG. 9 is a perspective view of the medicament delivery device in a medicament delivery state with the housing removed.

FIG. 7 shows a perspective view of the power assembly 27 and the manually operable assembly 30. FIG. 8 shows an exploded view of the power assembly 27 and the manually operable assembly 30. The rotator 27b has a cam surface 27i which is configured to interact with the axial protrusions 5b of the needle shield sleeve 5 when the needle shield sleeve 5 is moved distally in the housing 5 after the mixing procedure has been performed and the medicament delivery device 1 has obtained a medicament delivery state. Linear movement of the needle shield sleeve 5 is thereby converted to rotational motion of the rotator 27b.

The multi-chamber container 21 comprises a proximal chamber typically containing a freeze-dried medicament and a distal chamber which is separated from the proximal chamber by means of a first stopper, and which typically contains a liquid such as water. The multi-chamber container 21 may furthermore comprise a second stopper defining a distal wall of the distal chamber. The proximal end of the plunger rod 27a bears against a distal surface of the second stopper. The multi-chamber container 21 has a bypass channel between the proximal chamber and the distal chamber. In the initial locked state and the intermediate priming state of the medicament delivery device 1 the first stopper is positioned to block the bypass channel so that no liquid can pass from the distal chamber to the proximal chamber.

Figure 9:
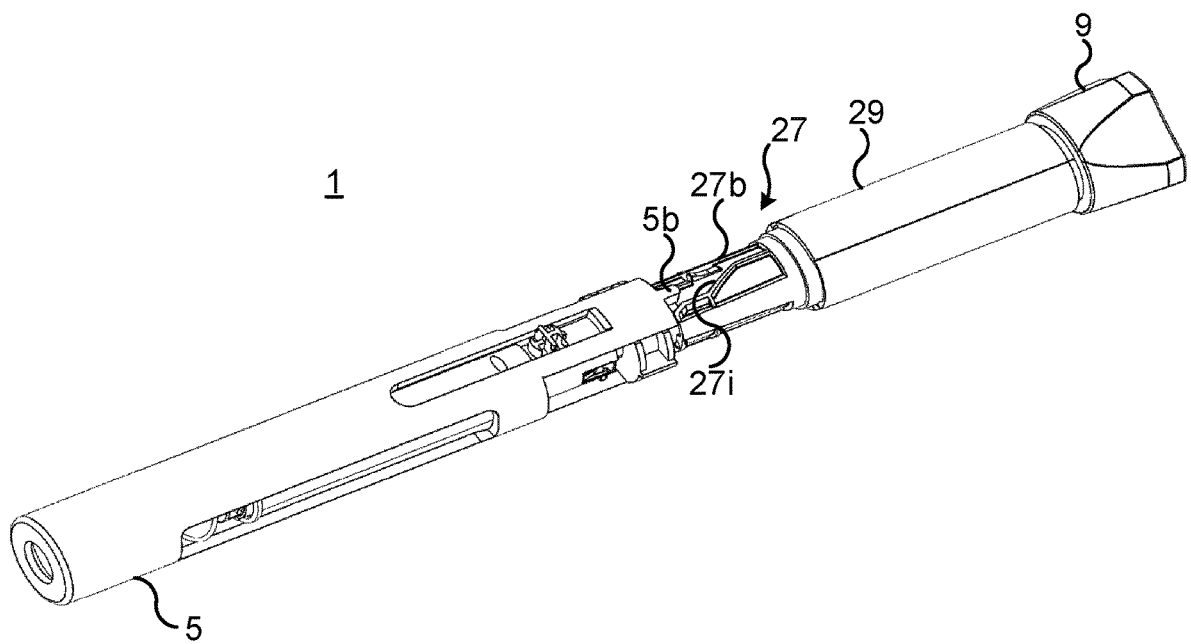

In order to perform mixing, the mixing knob 9 which is rotatable relative to the housing 3 in the intermediate priming state of the medicament delivery device 1 can be rotated one or more turns by a user. Since the mixing knob 9 is rotationally fixed relative to the sleeve member 29, rotation of the mixing knob 9 causes rotation of the sleeve member 29. Due to the treaded connection between the sleeve member 29 and the distal portion of the holding and release unit 27e, and since the holding and release unit 27e is rotationally fixed relative to the housing 3, the entire power assembly 27, including the holding and release unit 27e and the plunger rod 27a is moved in the proximal direction. The pitches of the first thread structure 29a and the second thread structure 27h define the speed with which the power assembly 27 is moved in the proximal direction and hence also the speed of the mixing/blending. As the plunger rod 27a is moved proximally, it pushes the second stopper forward in the proximal direction inside the multi-chamber container 21. This causes an increase in pressure inside the distal chamber, resulting in that the first stopper is moved in the proximal direction and eventually past the bypass channel such that the liquid contained in the distal chamber is able to flow into the proximal chamber via the bypass channel and mix with the freeze-dried medicament contained therein to form a blended compound or liquid medicament. When the mixing/blending has been completed, the medicament delivery device 1 obtains the medicament delivery state as shown in FIG. 9. In the medicament delivery state, the power assembly 27 has moved proximally in the housing 3 towards the distal end of the needle shield sleeve 5. The power assembly 27 has thus obtained a position in which distal movement of the needle shield sleeve 5 e.g. by pushing the needle shield sleeve 5 towards an injection site causes the axial protrusions 5b to move along the cam surface 27i of the rotator 27b and thereby cause rotation of the rotator 27b. As the rotator 27b is rotated, it releases the plunger rod 27a, causing it to move proximally further into the multi-chamber container 21 to thereby expel the mixed medicament through the proximal needle of the double-sided needle 17.

Figure 10:
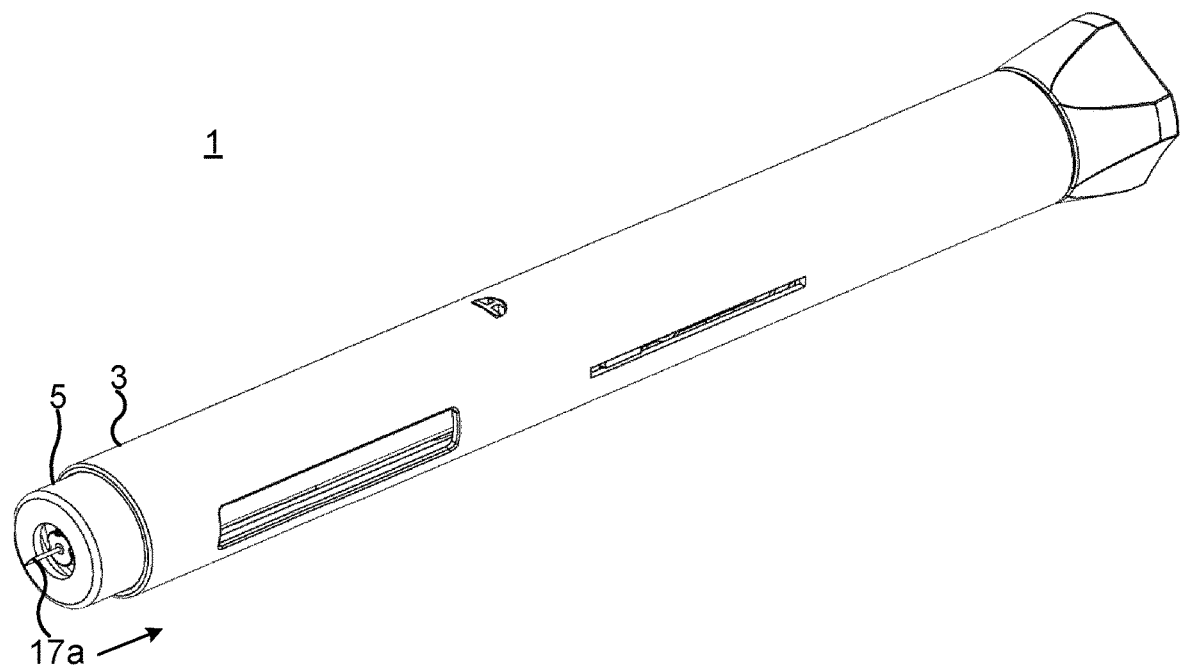
FIG. 10 is a perspective view of the medicament delivery device during medicament delivery.

FIG. 10 shows the medicament delivery device 1 as the needle shield sleeve 5 is moved proximally into the housing 3 to initiate medicament expulsion through the proximal needle 17a.

Figure 11:
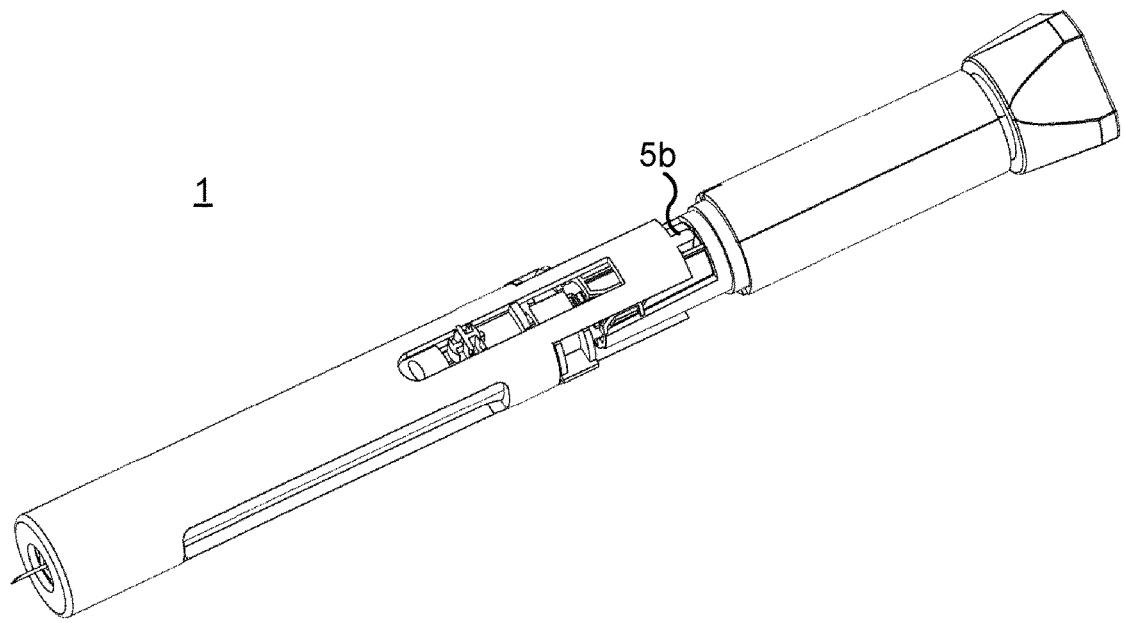
FIG. 11 shows the medicament delivery device in FIG. 10 with the housing removed.

FIG. 11 shows the medicament delivery device 1 in the state shown in FIG. 10 with the housing 3 removed to illustrate that the axial protrusions 5b of the needle shield sleeve 5 has moved along the cam surface 27i of the rotator 27b, which has caused the rotator 27b to rotate.

Figure 12:
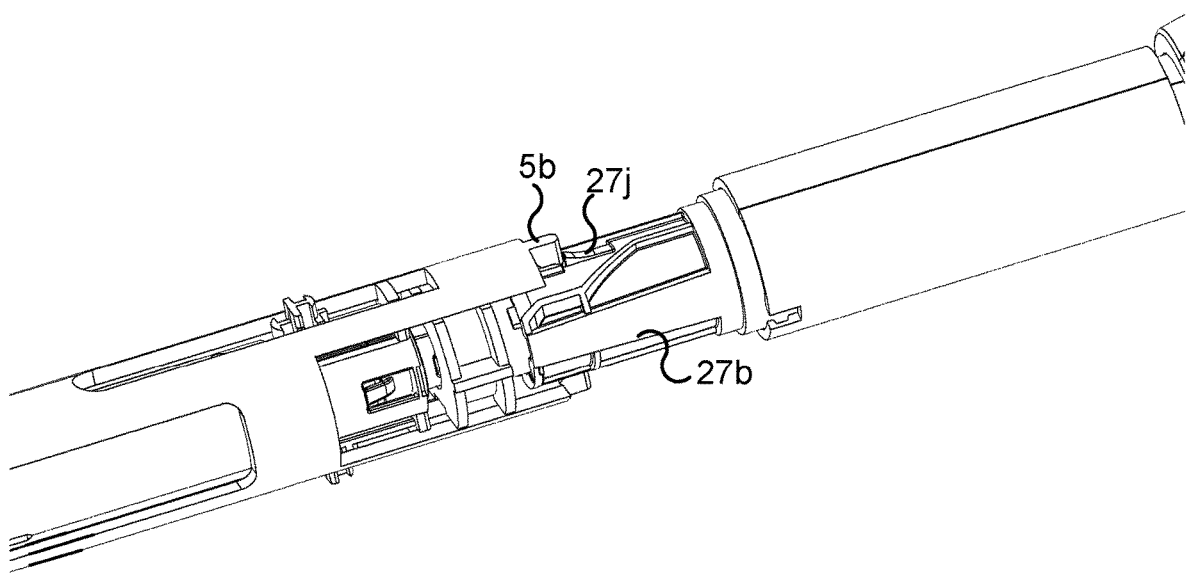
FIG. 12 is a close-up view of a portion of the medicament delivery device shown in a locked-out state after medicament delivery.
Figure 13:
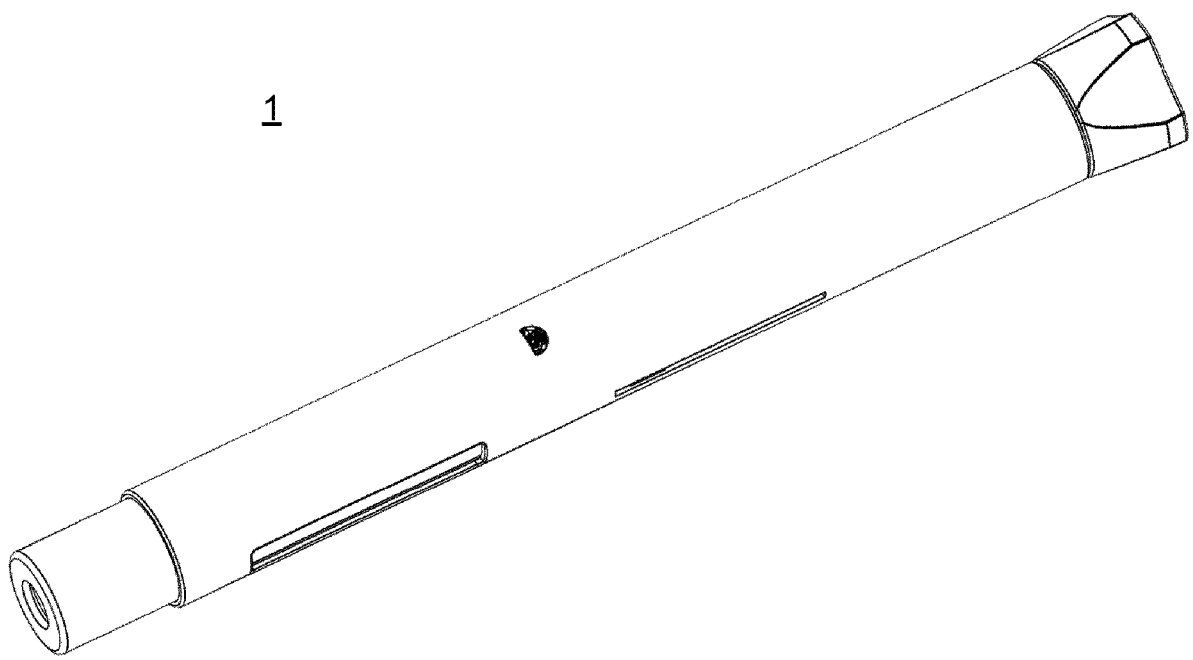
FIG. 13 depicts the medicament delivery device in the locked-out state.

When the medicament delivery device 1 and the proximally biased needle shield sleeve 5 is removed from the injection site after medicament administration, the needle shield sleeve 5 is moved proximally to the initial unlocked position, in which the needle shield sleeve 5 extends proximally from the housing 3. FIG. 12 shows a close-up view of a region of the rotator 27b. The rotator 27b is provided with lock-out structures 27j, for example snap-lock structures, which allow the axial protrusions 5b to move over them proximally when the needle shield sleeve 5 returns to the initial unlocked position, and which subsequently blocks the axial protrusions 5b from movement in the distal direction. The needle shield sleeve 5 is thereby locked out in the initial unlocked position, which is now a final locked position. The needle shield sleeve 5 may in this state not be pushed back into the housing 3, and hence the used proximal needle 17b cannot be exposed. FIG. 13 shows the medicament delivery device 1 in its locked-out state.

The invention claimed is:

1. A medicament delivery device comprising:
   a housing having a proximal end and a distal end;
   a multi-chamber container arranged in the housing;
   a container holder axially and rotationally fixed to the housing and in which the multi-chamber container is accommodated;
   a power assembly having accumulated energy, arranged in the housing and configured to act on the multi-chamber container for obtaining and delivering a blended compound inside the multi-chamber container, wherein a portion of the power assembly is axially fixed in the housing; and
   a manually operable assembly extending from the distal end of the housing and being connected with the power assembly,
   wherein the manually operable assembly is connected with the portion of the power assembly that is axially fixed in the housing by a threaded connection,
   wherein upon a manual movement of the manually operable assembly, the power assembly is forced to move towards the proximal end to pressurize the multi-chamber container, and
   wherein the medicament delivery device further comprises a needle shield sleeve slidably arranged in the housing, the needle shield sleeve being configured to interact with the power assembly to release the accumulated energy after the power assembly has been moved towards the proximal end.

2. The medicament delivery device according to claim 1, wherein the power assembly is a gas driven power assembly, an electromechanical driven power assembly, or a spring driven power assembly.

3. The medicament delivery device according to claim 1, wherein the manual movement of the manually operable assembly is a rotational movement and the threaded connection is configured to cause a linear movement of the power assembly towards the proximal end.

4. The medicament delivery device according to claim 1, comprising a resilient member arranged between a proximal end of the container holder and a proximal inner ledge of the needle shield sleeve.

5. The medicament delivery device according to claim 4, comprising a needle assembly disposed on the proximal end of the container holder and having a needle, wherein the multi-chamber container has a septum, and wherein the needle assembly is configured to be manually manipulated to move the needle toward the multi-chamber container in order for a distal end of the needle to pierce the septum.

6. The medicament delivery device according to claim 5, wherein the needle assembly comprises:
   a needle hub fixedly connected to the needle;
   an inner cap configured to move the needle hub;
   a retainer fixedly connected to the container holder and interactively engaged with the needle hub; and
   a manually operable outer cap configured to move the inner cap whereby the inner cap in turn moves the needle hub through the retainer and toward the multi-chamber container in order for the distal end of the needle to pierce the septum and whereby the inner cap together with the manually operable outer cap can be removed from the rest of the medicament delivery device.

7. The medicament delivery device according to claim 6, wherein the manually operable outer cap is configured to lock the needle shield sleeve in an initial locked position in which the needle shield sleeve is prevented from being axially moveable by a bias of the resilient member towards a proximal end of the medicament delivery device to an initial unlocked position.

8. The medicament delivery device according to claim 7, wherein a member on a distal end of the needle shield sleeve is releasably locked to a member of the manually operable assembly when the needle shield sleeve is in the initial locked position for preventing the manually operable assembly to be manually operated.

9. The medicament delivery device according to claim 8, wherein upon removal of the manually operable outer cap from the medicament delivery device, the needle shield sleeve is forced by the bias of the resilient member to move a predetermined distance in relation to the housing from the initial locked position to the initial unlocked position in which a predetermined portion of the needle shield sleeve protrudes from the proximal end of the housing.

10. The medicament delivery device according to claim 9, wherein a movement of the needle shield sleeve in relation to the housing from the initial unlocked position towards the distal end of the housing allows the member on the distal end of the needle shield sleeve to interact with a member of the power assembly to release the accumulated energy in the power assembly.

11. The medicament delivery device according to claim 1, wherein the multi-chamber container comprises a stopper and the power assembly comprises a plunger rod configured to be in contact with a distal surface of the stopper.

12. The medicament delivery device according to claim 11, wherein the power assembly further comprises a holding and release unit configured to interact with the plunger rod and the needle shield sleeve for holding and releasing the accumulated energy in the power assembly.

13. The medicament delivery device according to claim 12, wherein the holding and release unit is the portion of the power assembly that is axially fixed in the housing.

14. The medicament delivery device according to claim 1, wherein the housing comprises one or more radial openings, and wherein the container holder comprises one or more radially outward extending locking members such that the one or more radially outward extending locking members are configured to be received in the one or more radial openings.

15. A medicament delivery device comprising:
   a housing having a proximal end and a distal end;
   a multi-chamber container arranged in the housing;
   a container holder axially and rotationally fixed to the housing and in which the multi-chamber container is accommodated;
   a needle shield sleeve slidably arranged in the housing;
   a power assembly having accumulated energy, arranged in the housing and configured to act on the multi-chamber container for obtaining and delivering a blended compound inside the multi-chamber container, wherein a portion of the power assembly is axially fixed in the housing; and a manually operable assembly extending from the distal end of the housing and being connected with the power assembly, wherein the manually operable assembly is connected with the portion of the power assembly that is axially fixed in the housing by a threaded connection, wherein a rotational movement of the manually operable assembly by a user of the medicament delivery device causes linear movement of the power assembly towards the proximal end to pressurize the multi-chamber container, and wherein the needle shield sleeve is configured to interact with the power assembly to release the accumulated energy after the power assembly has moved towards the proximal end.

16. The medicament delivery device according to claim 15 further comprising a resilient member arranged between a proximal end of the container holder and a proximal inner ledge of the needle shield sleeve.

17. A medicament delivery device comprising:
a housing having a proximal end and a distal end;
a multi-chamber container arranged in a container holder axially fixed inside the housing;
a needle shield sleeve slidably arranged in the housing;
a needle assembly disposed on a proximal end of the container holder and having a needle,
a power assembly having accumulated energy, arranged in the housing and configured to act on the multi-chamber container for obtaining and delivering a blended compound inside the multi-chamber container, wherein a portion of the power assembly is axially fixed in the housing; and a manually operable assembly extending from the distal end of the housing and being connected with the power assembly, wherein the manually operable assembly is connected with the portion of the power assembly that is axially fixed in the housing by a threaded connection, wherein a rotational movement of the manually operable assembly by a user of the medicament delivery device causes linear movement of the power assembly towards the proximal end to pressurize the multi-chamber container, and wherein the needle shield sleeve is configured to interact with the power assembly to release the accumulated energy after the power assembly has moved towards the proximal end.

18. The medicament delivery device according to claim 17, wherein the multi-chamber container has a septum, and the needle assembly is configured such that manual manipulation by the user moves the needle toward the multi-chamber container to cause a distal end of the needle to pierce the septum.

19. The medicament delivery device according to claim 18, wherein the needle assembly comprises:
a needle hub fixedly connected to the needle;
an inner cap configured to move the needle hub;
a retainer fixedly connected to the container holder and interactively engaged with the needle hub;
a manually operable outer cap configured to move the inner cap which moves the needle hub through the retainer and toward the multi-chamber container so that the distal end of the needle pierces the septum,
wherein the inner cap together with the manually operable outer cap can be removed from the rest of the medicament delivery device.

* * * * *